US012570596B2

(12) United States Patent
Kim et al.

(10) Patent No.: US 12,570,596 B2
(45) Date of Patent: Mar. 10, 2026

(54) PROCESS FOR PRODUCING ACRYLIC ACID

(71) Applicant: LG CHEM, LTD., Seoul (KR)

(72) Inventors: Eunkyo Kim, Daejeon (KR); Mi Kyung Kim, Daejeon (KR); Joon Ho Shin, Daejeon (KR); Hyebin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 718 days.

(21) Appl. No.: 17/921,168

(22) PCT Filed: Oct. 27, 2021

(86) PCT No.: PCT/KR2021/015176
§ 371 (c)(1),
(2) Date: Oct. 25, 2022

(87) PCT Pub. No.: WO2022/114546
PCT Pub. Date: Jun. 2, 2022

(65) Prior Publication Data
US 2023/0167044 A1 Jun. 1, 2023

(30) Foreign Application Priority Data

Nov. 24, 2020 (KR) ........................ 10-2020-0159080

(51) Int. Cl.
*C07C 51/487* (2006.01)
(52) U.S. Cl.
CPC .................................. *C07C 51/487* (2013.01)
(58) Field of Classification Search
CPC ..................................................... C07C 51/487
See application file for complete search history.

(56) References Cited

U.S. PATENT DOCUMENTS

| | | |
|---|---|---|
| 8,198,481 B2 | 6/2012 | Kuppinger et al. |
| 9,029,596 B2 | 5/2015 | Yoshida et al. |
| 9,758,463 B1 | 9/2017 | Kamei et al. |
| 9,783,479 B1 | 10/2017 | Jain et al. |
| 10,344,108 B2 | 7/2019 | Godlewski et al. |
| 10,562,877 B2 | 2/2020 | Yazdanpanah et al. |
| 2002/0035287 A1 | 3/2002 | Otsuka et al. |
| 2010/0113822 A1 | 5/2010 | Craciun et al. |
| 2011/0089016 A1 | 4/2011 | Winkelaar et al. |
| 2017/0253553 A1 | 9/2017 | Kamei et al. |

FOREIGN PATENT DOCUMENTS

| | | |
|---|---|---|
| EP | 2066611 B1 | 6/2016 |
| JP | 2014-189510 | 10/2014 |
| JP | 5654615 | 1/2015 |
| JP | 2016-175840 | 10/2016 |
| JP | 6272493 | 1/2018 |
| JP | 6434400 | 12/2018 |
| KR | 10-2002-0023133 A | 3/2002 |
| KR | 10-2017-0095068 | 8/2017 |
| KR | 10-2017-0113177 | 10/2017 |
| KR | 10-2019-0018715 | 2/2019 |
| WO | 2005-095320 | 10/2005 |
| WO | 2016-026761 | 2/2016 |

OTHER PUBLICATIONS

KR20170095068A (Lee; IDS reference; English language machine translation) (Year: 2017).*

* cited by examiner

*Primary Examiner* — Amy C Bonaparte
*Assistant Examiner* — Derek Rhoades
(74) *Attorney, Agent, or Firm* — Bryan Cave Leighton Paisner LLP

(57) ABSTRACT

Provided is a process for producing acrylic acid, the process comprising: (step 1) preparing a first aqueous lactic acid solution by diluting a lactic acid raw material with water; (step 2) heat exchanging the first aqueous lactic acid solution to form a vaporized second lactic acid vapor and an unvaporized third aqueous lactic acid solution; (step 3) including the unvaporized third aqueous lactic acid solution in the aqueous solution of the step 1; and (step 4) supplying and absorbing an absorption liquid to the vaporized second lactic acid vapor to form an absorbed fourth aqueous lactic acid solution and an unabsorbed fifth lactic acid vapor, wherein the absorption liquid is water or an aqueous lactic acid solution.

10 Claims, 2 Drawing Sheets

【FIG. 1】
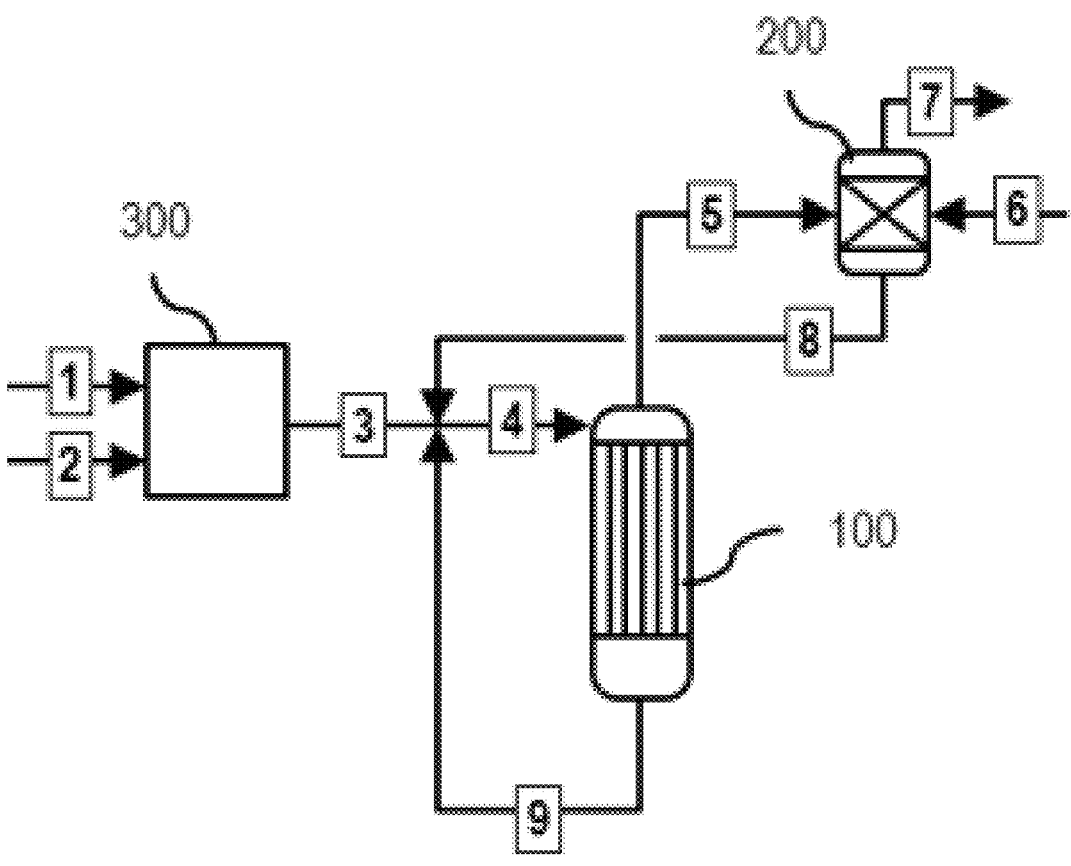
【FIG. 2】
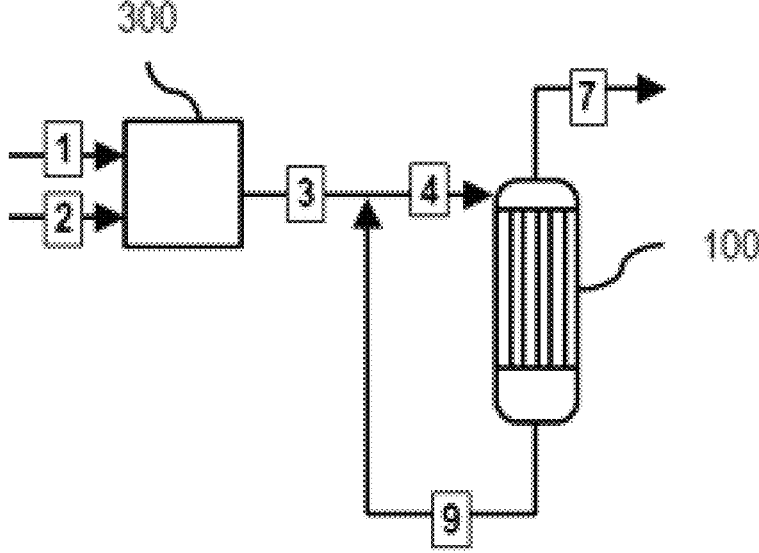

【FIG. 3】
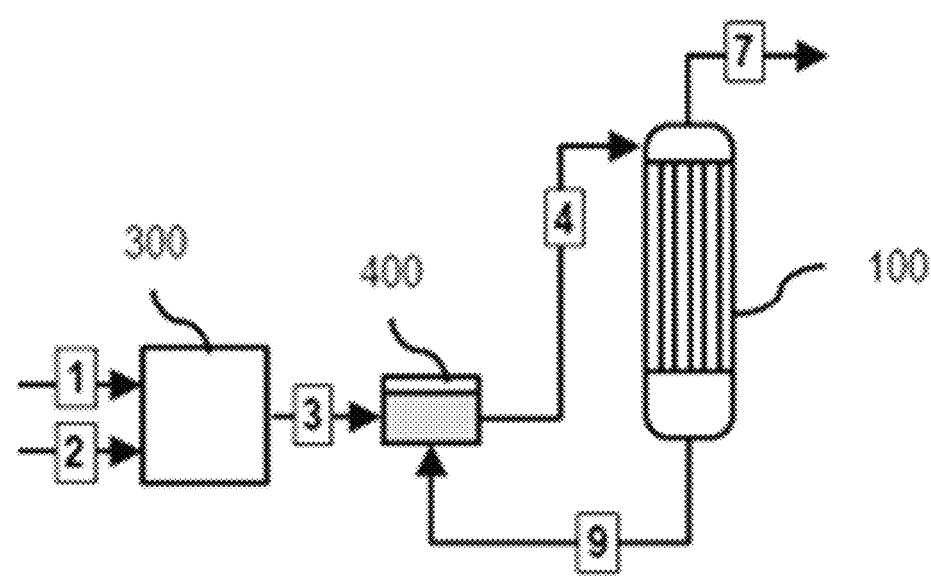

PROCESS FOR PRODUCING ACRYLIC ACID

CROSS-REFERENCE TO RELATED APPLICATION(S)

This application is a National Stage Application of International Application No. PCT/KR2021/015176 filed on Oct. 27, 2021, which claims priority to and the benefits of Korean Patent Application No. 10-2020-0159080, filed with the Korean Intellectual Property Office on Nov. 24, 2020, the entire contents of which are incorporated herein by reference.

TECHNICAL FIELD

The present application relates to a process for producing acrylic acid.

BACKGROUND

Acrylic acid has been generally produced through an oxidative dehydrogenation reaction of propylene, and demands on acrylic acid have increased as a raw material of super absorbent polymers, paints, adhesives and the like. Particularly, super absorbent polymers are used as hygiene products such as diapers.

So far, a considerable number of chemical products have been produced using raw materials derived from fossil raw materials such as coal or petroleum. However, using recyclable bio-derived resources as a carbon source has recently received attention as a substitute for existing fossil raw materials in terms of preventing global warming and protecting the environment. For example, development of methods using biomass resources including starch-based biomass such as corn or wheat, carbohydrate-based biomass such as sugar cane, cellulose-based biomass such as residue of rapeseed or rice straw, and the like as a raw material has been attempted.

Studies on breaking from existing petrochemical-based manufacturing processes and producing chemical products based on environmental-friendly raw materials to obtain excellent properties in terms of environmental protection while obtaining sustainability are recently in progress.

One type of reaction producing other chemical products from lactic acid can include a gas-phase reaction in which a raw material including lactic acid is evaporated and brought into contact with a catalyst in a gaseous state to obtain a product. For example, as a technology of producing acrylic acid using lactic acid, a gas-phase dehydration reaction using a solid catalyst is known, and the dehydration reaction of lactic acid is mainly studied as a gas-phase reaction.

Lactic acid is a substance that polymerizes as an esterification reaction that occurs in a liquid phase without a catalyst in the absence of water, and reacts as a lactic acid oligomer as lactic acid is concentrated and a concentration thereof increases. Dehydration occurs as lactic acid is oligomerized, and an oligomerization reaction of lactic acid occurs as the lactic acid is concentrated without water.

When the lactic acid oligomer is introduced to a reactor for producing acrylic acid, fouling occurs in the reactor and the reaction yield decreases, and therefore, studies on a method to decrease the content of lactic acid oligomer for producing acrylic acid is in progress.

Among them, lactic acid is introduced to a vaporizer in an aqueous lactic acid solution state in order to reduce the lactic acid oligomer content, however, water with a low boiling point is vaporized first and then lactic acid is vaporized in the vaporizer, and a problem of producing a lactic acid oligomer still occurs as the lactic acid is concentrated in the liquid phase during the vaporization.

In addition, a distillation tower that separates using a boiling point difference so as not to include an oligomer in a vaporized aqueous lactic acid solution can be used, however, an oligomerization reaction of lactic acid occurs herein as well concentrating the lactic acid oligomer, and a problem of increasing a temperature of a low portion of the distillation tower occurs.

Accordingly, in view of the above, studies to decrease a lactic acid oligomer content and increasing a produced acrylic acid yield are in progress.

Prior Art Documents

International Patent Publication No. WO 2005/095320 A1

BRIEF DESCRIPTION

Technical Problem

The present application is directed to providing a process for producing acrylic acid.

Technical Solution

One embodiment of the present application provides a process for producing acrylic acid, the process including a step 1 of preparing a first aqueous lactic acid solution by diluting a lactic acid raw material with water; a step 2 of heat exchanging the first aqueous lactic acid solution to form a vaporized second lactic acid vapor and an unvaporized third aqueous lactic acid solution; a step 3 of including the unvaporized third aqueous lactic acid solution in the aqueous solution of the step 1; and a step 4 of supplying and absorbing an absorption liquid to the vaporized second lactic acid vapor to form an absorbed fourth aqueous lactic acid solution and an unabsorbed fifth lactic acid vapor, wherein the absorption liquid is water or an aqueous lactic acid solution.

Advantageous Effects

By adding a process of supplying an absorption liquid to a gas-phase aqueous lactic acid solution vaporized through a heat exchanger in a process for producing acrylic acid according to one embodiment of the present application, a lactic acid oligomer included in the gas-phase aqueous lactic acid solution is absorbed, and a content of the oligomer is reduced in the aqueous lactic acid solution before it is supplied to a reactor feed.

Particularly, by absorbing the oligomer included in the lactic acid vapor (second lactic acid vapor), which is vaporized by going through a heat exchanger, through the absorption process, a content of the lactic acid oligomer is reduced in the lactic acid vapor reducing a fouling phenomenon in the vaporizer and the reaction unit, and by including a high-content lactic acid monomer, a yield of produced acrylic acid increases and loss is minimized, increasing economic feasibility.

DESCRIPTION OF THE DRAWINGS

FIG. 1 is a schematic diagram illustrating a process for producing acrylic acid according to one embodiment of the present application.

FIG. 2 is a schematic diagram illustrating a process for producing acrylic acid according to Comparative Example 1 of the present application.

FIG. 3 is a schematic diagram illustrating a process for producing acrylic acid according to Comparative Example 2 of the present application.

REFERENCE NUMERALS

100: Heat Exchanger
200: Absorption Device
300: Dilution Tank
400: Decomposition Tank
1: Lactic Acid Raw Material
2: Water
3: Liquid Aqueous Lactic Acid Solution
4: First Aqueous Lactic Acid Solution
5: Second Lactic Acid Vapor
6: Absorption Liquid
7: Fifth Lactic Acid Vapor
8: Fourth Aqueous Lactic Acid Solution
9: Third Aqueous Lactic Acid Solution (Liquid Circulation Flow)

DETAILED DESCRIPTION

Hereinafter, the present specification will be described in more detail.

In the present specification, a description of a certain part "including" certain constituents means capable of further including other constituents, and does not exclude other constituents unless particularly stated on the contrary.

In the present specification, 'p to q' means a range of 'greater than or equal to p and less than or equal to q'.

Hereinafter, embodiments of the present disclosure will be described in detail with reference to accompanying drawings so that those having common knowledge in the art can readily implement the present disclosure. However, the present disclosure can be embodied in various different forms, and is not limited to the embodiments described herein.

One embodiment of the present application provides a process for producing acrylic acid, the process including a step 1 of preparing a first aqueous lactic acid solution by diluting a lactic acid raw material with water; a step 2 of heat exchanging the first aqueous lactic acid solution to form a vaporized second lactic acid vapor and an unvaporized third aqueous lactic acid solution; a step 3 of including the unvaporized third aqueous lactic acid solution in the aqueous solution of the step 1; and a step 4 of supplying and absorbing an absorption liquid to the vaporized second lactic acid vapor to form an absorbed fourth aqueous lactic acid solution and an unabsorbed fifth lactic acid vapor, wherein the absorption liquid is water or an aqueous lactic acid solution.

By adding the process of supplying an absorption liquid to the gas-phase second lactic acid vapor vaporized through a heat exchanger in the process for producing acrylic acid according to one embodiment of the present application, a lactic acid oligomer included in the gas-phase second lactic acid vapor is absorbed, and a fifth lactic acid vapor is supplied after reducing a content of the oligomer in the second lactic acid vapor before it is supplied to a reactor feed.

Particularly, by absorbing the oligomer included in the lactic acid vapor (second lactic acid vapor), which is vaporized by going through a heat exchanger, through the absorption process, a content of the lactic acid oligomer is reduced in the lactic acid vapor, reducing a fouling phenomenon in the vaporizer and the reaction unit, and by including a high-content lactic acid monomer, a yield of produced acrylic acid increases and loss is minimized, increasing economic feasibility.

One embodiment of the present application provides the step 1 of preparing a first aqueous lactic acid solution by diluting a lactic acid raw material with water.

In one embodiment of the present application, the lactic acid raw material can include water, lactic acid, and a lactic acid oligomer.

In the present application, the lactic acid is an organic compound having an asymmetric carbon atom to which four atomic groups of a carboxyl group, a hydroxyl group, a methyl group and hydrogen bond, and includes both D-lactic acid and L-lactic acid, and can mean a single lactic acid monomer.

In the present application, a lactic acid oligomer means a material obtained by lactic acid reacting to each other to form a dimer, a trimer and the like, and the lactic acid oligomer can mean a dimer to a 100-mer of lactic acid.

Lactic acid is a substance that polymerizes through an esterification reaction in a liquid phase without a catalyst even in the absence of water, and substances formed through a polymerization reaction of lactic acid can all be expressed as a lactic acid oligomer. In other words, all substances formed through a polymerization reaction of lactic acid other than a single lactic acid monomer can be defined as a lactic acid oligomer.

In one embodiment of the present application, the step 1 is a step of diluting with water in a lactic acid raw material state, and can mean a step for minimizing an oligomer by increasing a content of water produced during an equilibrium reaction of lactic acid oligomer formation.

In one embodiment of the present application, the first aqueous lactic acid solution includes water and a lactic acid raw material, the lactic acid raw material includes lactic acid and a lactic acid oligomer, and the lactic acid raw material is included in greater than or equal to 30 parts by weight and less than or equal to 99 parts by weight based on 100 parts by weight of the first aqueous lactic acid solution.

In another embodiment, the lactic acid raw material can be included in greater than or equal to 50 parts by weight and less than or equal to 99 parts by weight, preferably greater than or equal to 60 parts by weight and less than or equal to 99 parts by weight, and more preferably greater than or equal to 70 parts by weight and less than or equal to 99 parts by weight based on 100 parts by weight of the first aqueous lactic acid solution.

In one embodiment of the present application, the first aqueous lactic acid solution can mean an aqueous lactic acid solution including all of the first aqueous lactic acid solution prepared by diluting the lactic acid raw material in the step 1, and a liquid circulation flow of the third aqueous lactic acid solution not vaporized in the heat exchanger and a liquid circulation flow of the absorption liquid used in the absorption process to be described later.

In the process for producing acrylic acid provided in one embodiment of the present application, a ratio of the lactic acid:lactic acid oligomer in the first aqueous lactic acid solution is from 1:99 to 20:80.

In another embodiment, a ratio of the lactic acid:lactic acid oligomer in the first aqueous lactic acid solution can satisfy a ratio of 1:99 to 20:80, 3:97 to 20:80 and 5:95 to 20:80.

As described above, the first aqueous lactic acid solution is an aqueous solution in which three types of aqueous lactic acid solutions are mixed, and since the ratio of the lactic acid oligomer in the third aqueous lactic acid solution included through a liquid circulation flow is high, the ratio of the lactic acid oligomer can be high in the first aqueous lactic acid solution as above.

FIG. 1 is a schematic diagram illustrating the process for producing acrylic acid according to one embodiment of the present application. Particularly, the step 1 can be a step of preparing the aqueous solution (4) of the step 1 including all of the liquid aqueous lactic acid solution (3) produced by diluting the lactic acid raw material with water, a liquid flow (9) of the unvaporized third aqueous lactic acid solution produced in the step 2 to be described later, and the absorbed fourth aqueous lactic acid solution (8) produced in the step 4 to be described later.

In other words, by circulating all the third aqueous lactic acid solution and the fourth aqueous lactic acid solution in each step back to the step 1 by a liquid flow as above, the amount of lost lactic acid can be minimized.

As described above, the step 1 can correspond to a step of diluting the lactic acid raw material with water before it is introduced to the step of heat exchanging, the step 2, to be described later.

One embodiment of the present application provides the step 2 of heat exchanging the first aqueous lactic acid solution to form a vaporized second lactic acid vapor and an unvaporized third aqueous lactic acid solution.

Herein, the step 2 can include a process of heat exchanging through a heat exchanger.

In one embodiment of the present application, the heat exchanger can be one or more selected from the group consisting of a falling film evaporator, a wiped film evaporator, a thermosyphon, and a forced circulation evaporator, but is not limited thereto as long as it is capable of vaporizing the first aqueous lactic acid solution.

In other words, in one embodiment of the present application, the step 2 is a step of vaporizing the aqueous solution of the step 1. A reaction for producing acrylic acid from lactic acid is mainly conducted as a gas-phase reaction, and accordingly, the step 2 can be a step relating to a process of vaporizing the liquid aqueous solution of the step 1 to a gas phase.

The process for producing acrylic acid according to one embodiment of the present application includes a circulation process, and the aqueous solution of the step 1 includes the first aqueous lactic acid solution in the initial process of normal state. When conducting the circulation process after that, the aqueous solution of the step 1 can include one or more of the first aqueous lactic acid solution, the third aqueous lactic acid solution to be described later, and the fourth aqueous lactic acid solution to be described later.

In one embodiment of the present application, the vaporized second lactic acid vapor and the unvaporized third aqueous lactic acid solution are formed by vaporizing the aqueous solution of the step 1, and the vaporized second lactic acid vapor maintains a low lactic acid oligomer content compared to the unvaporized third aqueous lactic acid solution.

In the step of vaporizing the liquid aqueous solution of the step 1 through the heat exchanger, water having a lower boiling point included in the aqueous solution of the step 1 is vaporized first and lactic acid having a relatively higher boiling point is vaporized later, and as the water is vaporized in the vaporization, lactic acid is concentrated forming a lactic acid oligomer. When the lactic acid oligomer is included in the vaporized second lactic acid vapor, it can be introduced to a reactor later on causing an occurrence of fouling in the reactor and a problem of reducing a reaction yield of produced acrylic acid, and therefore, lowering a content of the lactic acid oligomer in the vaporized second lactic acid vapor in the step 4 to be described later is a characteristic of the present disclosure.

In other words, the lactic acid oligomer content is high even in the second lactic acid vapor state vaporized through the step 2, which can cause a problem, and the present application includes the step 4 of absorbing lactic acid oligomer through an absorption device in order to reduce the lactic acid oligomer content in the second lactic acid vapor.

In one embodiment of the present application, the unvaporized third aqueous lactic acid solution is recycled back to the aqueous solution of the step 1 from the heat exchanger through a liquid circulation flow, and accordingly, acrylic acid can be produced without loss of the lactic acid raw material.

In the process for producing acrylic acid provided in one embodiment of the present application, the heat exchanger has an inner pressure of greater than or equal to 0.3 bar and less than or equal to 3 bar and an inner temperature of higher than or equal to 150° C. and lower than or equal to 300° C.

In another embodiment, the heat exchanger can have an inner pressure of greater than or equal to 0.3 bar and less than or equal to 3.0 bar, preferably greater than or equal to 0.5 bar and less than or equal to 2.5 bar, and more preferably greater than or equal to 1.0 bar and less than or equal to 1.5 bar.

In another embodiment, the heat exchanger can have an inner temperature of 200° C. or higher, preferably 210° C. or higher and more preferably 215° C. or higher, and can be 300° C. or lower.

By adjusting the pressure of the heat exchanger to the above-mentioned range, the temperature of the heat exchanger can be properly maintained in the above-mentioned range, and a pressure difference with a reactor can be reduced as well later on properly forming capacity of a compressor for the subsequent processes. In addition, by adjusting the temperature of the heat exchanger to the above-mentioned range, the aqueous solution of the step 1 included inside the heat exchanger can be vaporized, and a yield of acrylic acid can increase since the lactic acid raw material is not decomposed.

In the process for producing acrylic acid provided in one embodiment of the present application, the second lactic acid vapor includes water and a lactic acid raw material, the lactic acid raw material includes lactic acid and a lactic acid oligomer, and the lactic acid raw material is included in greater than or equal to 15 parts by weight and less than or equal to 80 parts by weight based on 100 parts by weight the second lactic acid vapor.

In another embodiment, the lactic acid raw material can be included in greater than or equal to 15 parts by weight and less than or equal to 80 parts by weight, preferably greater than or equal to 17 parts by weight and less than or equal to 75 parts by weight, and more preferably greater than or equal to 20 parts by weight and less than or equal to 60 parts by weight based on 100 parts by weight of the second lactic acid vapor.

In the process for producing acrylic acid provided in one embodiment of the present application, a ratio of the lactic acid:lactic acid oligomer in the second lactic acid vapor is from 80:20 to 95:5. Herein, the ratio can mean a weight ratio.

In another embodiment, a ratio of the lactic acid:lactic acid oligomer in the second lactic acid vapor can satisfy a range of 80:20 to 95:5, 81:19 to 93:7 and 82:18 to 90:10.

The second lactic acid vapor is included in a reactor of the process of producing acrylic acid later on, and by the ratio of the lactic acid raw material and the lactic acid included in the lactic acid raw material in the second lactic acid vapor state vaporized through the step 2 satisfying the above-mentioned range, the amount of water introduced to the reactor and the amount of introduction are suitable. After that, the second lactic acid vapor can have a minimized lactic acid oligomer ratio through the absorption process to be described later.

In one embodiment of the present application, the unvaporized third aqueous lactic acid solution can be recycled back to the aqueous solution of the step 1 through a liquid flow, and the first aqueous lactic acid solution can include the unvaporized third aqueous lactic acid solution.

The third aqueous lactic acid solution forms a lactic acid oligomer through an oligomerization reaction of the concentrated lactic acid, and is recirculated without being vaporized. The third aqueous lactic acid solution can include the lactic acid oligomer in greater than or equal to 90 parts by weight and less than or equal to 99 parts by weight based on 100 parts by weight of the third aqueous lactic acid solution.

After that, a process of introducing water to the first aqueous lactic acid solution including the third aqueous lactic acid solution (that is, this can be defined as the aqueous solution of the step 1) for dilution is conducted, and through an equilibrium reaction, the content of the lactic acid oligomer in the aqueous lactic acid solution introduced into the heat exchanger can be reduced as much as possible.

FIG. 1 is a schematic diagram illustrating the process for producing acrylic acid according to one embodiment of the present application. Particularly, the step 2 is a step of heat exchanging the aqueous solution of the step 1 (4) to form the vaporized second lactic acid vapor (5) and the unvaporized third aqueous lactic acid solution (9), and the step 3 can mean to represent a liquid circulation flow including the unvaporized third aqueous lactic acid solution (9) in the aqueous solution of the step 1.

One embodiment of the present application can include the step 4 of supplying and absorbing an absorption liquid to the vaporized second lactic acid vapor to form an absorbed fourth aqueous lactic acid solution and an unabsorbed fifth lactic acid vapor.

In one embodiment of the present application, the absorption liquid is supplied to the second lactic acid vapor to form an absorbed fourth aqueous lactic acid solution having a high lactic acid oligomer content, and through the process of circulating the fourth aqueous lactic acid solution back to the step 1, an economically superior process can be provided without loss of the raw material. In addition, the unabsorbed fifth lactic acid vapor is formed by the absorption process that is the step 4, and accordingly, a lactic acid oligomer content in the fifth lactic acid vapor is minimized, and the reaction yield can increase by using the fifth lactic acid vapor in the process of producing acrylic acid to be conducted later.

In other words, the lactic acid oligomer content is high even in the second lactic acid vapor state vaporized through the step 2, which can cause a problem, and the present application includes the step 4 of absorbing lactic acid oligomer through an absorption device in order to reduce the lactic acid oligomer content in the second lactic acid vapor.

In one embodiment of the present application, the absorbed fourth aqueous lactic acid solution can include water and a lactic acid raw material, and the fourth aqueous lactic acid solution can be recycled back to the aqueous solution of the step 1 by a circulation flow along with the absorption liquid.

In the process for producing acrylic acid provided in one embodiment of the present application, the absorption device can be one or more selected from the group consisting of a drum, a spray drum, a packing column, and a tray column.

In one embodiment of the present application, the absorption device can be a packing or multi-level absorption tower.

The absorption process is a process of absorbing and decomposing the lactic acid oligomer in the second lactic acid vapor to increase a lactic acid monomer content. An absorption liquid can be used in the absorption process, and the absorption liquid can be water or an aqueous lactic acid solution.

Through the absorption process, the process for producing acrylic acid according to the present application adds a process of reducing the lactic acid oligomer content once more, which reduces an occurrence of fouling in a reactor for the final process of producing acrylic acid, increases the reaction yield, and maximizes economic feasibility by minimizing loss of lactic acid through increasing the content of the vaporized lactic acid with respect to the amount of the lactic acid raw material introduced.

In the process for producing acrylic acid provided in one embodiment of the present application, the fifth lactic acid vapor can be famed through the absorption process, and the fifth lactic acid vapor includes water and a lactic acid raw material, and the lactic acid raw material includes lactic acid and a lactic acid oligomer.

The lactic acid raw material is included in greater than or equal to 10 parts by weight and less than or equal to 80 parts by weight based on 100 parts by weight of the fifth lactic acid vapor.

In another embodiment, the lactic acid raw material can be included in greater than or equal to 15 parts by weight and less than or equal to 80 parts by weight, preferably greater than or equal to 17 parts by weight and less than or equal to 80 parts by weight, and more preferably greater than or equal to 20 parts by weight and less than or equal to 75 parts by weight based on 100 parts by weight of the fifth lactic acid vapor.

The fifth lactic acid vapor is a final aqueous lactic acid solution in a vaporized state before producing acrylic acid, and by the lactic acid raw material content satisfying the above-mentioned range in the fifth lactic acid vapor, the introduced amount of the lactic acid raw material itself is suitable, and by properly adjusting the water content to a proper range, excellent economic feasibility is obtained in the subsequent process of producing acrylic acid.

In the process for producing acrylic acid provided in one embodiment of the present application, a ratio of the lactic acid:lactic acid oligomer in the fifth lactic acid vapor is from 100:0 to 90:10.

In another embodiment, a ratio of the lactic acid:lactic acid oligomer in the fifth lactic acid vapor can satisfy a range of 100:0 to 90:10, preferably 100:0 to 95:5 and more preferably 100:0 to 97:3.

In other words, the process for producing acrylic acid according to the present disclosure breaks from existing petrochemical-based manufacturing processes and produces acrylic acid based on lactic acid, an environmental-friendly raw material, and as a result, excellent properties are obtained in terms of environmental protection while obtaining sustainability. The fifth lactic acid vapor is a lactic acid vapor in a final state introduced to a reactor, and through such an absorption process, the process for producing acrylic acid according to the present application adds the process of reducing the lactic acid oligomer content once more, and an occurrence of fouling in the reactor for the final process of producing final acrylic acid can be reduced, and the reaction yield can increase.

In the process for producing acrylic acid provided in one embodiment of the present application, the absorption device has an inner pressure of greater than or equal to 0.3 bar and less than or equal to and an inner temperature of higher than or equal to 100° C. and lower than or equal to 230° C.

In another embodiment, the absorption device can have an inner pressure of greater than or equal to 0.3 bar and less than or equal to 3.0 bar, preferably greater than or equal to 0.5 bar and less than or equal to 2.5 bar, and more preferably greater than or equal to 1.0 bar and less than or equal to 1.5 bar.

By adjusting the pressure of the absorption device to the above-mentioned range, a pressure difference with a reactor can be reduced later on, and capacity of a compressor for the subsequent processes can be properly formed.

In another embodiment, the absorption device can have an inner temperature of higher than or equal to 100° C. and lower than or equal to 230° C., preferably higher than or equal to 110° C. and lower than or equal to 220° C., and more preferably higher than or equal to 120° C. and lower than or equal to 200° C.

In the process for producing acrylic acid provided in one embodiment of the present application, the absorption liquid is supplied and absorbed to the vaporized second lactic acid vapor to form the absorbed fourth aqueous lactic acid solution and the unabsorbed fifth lactic acid vapor, and the fourth aqueous lactic acid solution is included in the aqueous solution of the step 1.

into contact with a collection liquid, and after going through a purification process such as extraction, distillation and crystallization, high purity acrylic acid can be obtained. Produced acrylic acid is widely used as a raw material of absorbent polymers, paints, adhesives or the like.

Hereinafter, examples of the present disclosure will be described in detail so that those having common knowledge in the art can readily implement the present disclosure. However, the present disclosure can be embodied in various different forms, and is not limited to the examples described herein.

EXAMPLES

The following examples and comparative examples were simulated by Aspen Plus of Aspen Technology Inc.

Comparative Example 1

As identified in FIG. 2, a purified lactic acid raw material was diluted in water to prepare a liquid aqueous lactic acid solution (3) having 40% of the lactic acid raw material, and the aqueous solution was introduced to a heat exchanger. 2% thereof was vaporized in the heat exchanger, and the liquid not vaporized was recirculated (7). The flow rate of the recirculated liquid was approximately 50 times that of the liquid aqueous lactic acid solution (3), and the recirculated liquid flow and the heat exchanger IN are introduced to the heat exchanger. After that, the gas-phase lactic acid stream vaporized in the heat exchanger was used as a reactor feed.

The heat exchanger had a pressure of 1.5 bar, a temperature of 217° C. and a calorie (amount of heat) of 0.5 MMkcal/hr.

The operation process of Comparative Example 1 is shown in FIG. 2, and as illustrated in FIG. 2, flow rates of the liquid aqueous lactic acid solution (3), the aqueous solution (4) of the step 1, the third aqueous lactic acid solution (9) and the fifth lactic acid vapor (7), and a composition of each stream are as shown in the following Table 1.

TABLE 1

| Stream No. | | 1 | 2 | 3 | 4 | 7 | 9 |
|---|---|---|---|---|---|---|---|
| Flow Rate (kg/hr) | | 455 | 545 | 1000 | 51000 | 1000 | 50000 |
| Composition | Water | 0.149 | 1.000 | 0.602 | 0.018 | 0.607 | 0.006 |
| | Lactic Acid | 0.612 | 0.000 | 0.380 | 0.114 | 0.33 | 0.108 |
| | Lactic Acid Oligomer | 0.239 | 0.000 | 0.018 | 0.869 | 0.056 | 0.886 |

In other words, as described above, the first aqueous lactic acid solution of the step 1 can include the fourth aqueous lactic acid solution.

FIG. 1 is a schematic diagram illustrating the process for producing acrylic acid according to one embodiment of the present application. Particularly, the step 4 can include the process of supplying the vaporized second lactic acid vapor (5) to the absorption device (200), and absorbing lactic acid oligomer through the absorption liquid (6), and as a result, the absorbed fourth aqueous lactic acid solution (8) is circulated to the step 1 through a circulation flow to form the aqueous solution (4) of the step 1, and finally, the unabsorbed fifth lactic acid vapor (7) with a minimized lactic acid oligomer content is included in the final process of producing acrylic acid.

The production process of the present disclosure is particularly useful for synthesizing acrylic acid, and specifically, the vapor composition including lactic acid obtained in the present disclosure can be brought into contact with a dehydration catalyst to prepare acrylic acid. A produced reaction gas is collected and liquefied by cooling or brining

Comparative Example 2

As shown in FIG. 3, a purified lactic acid raw material (1) was diluted in water (2) to prepare a liquid aqueous lactic acid solution (3) having 40% of the lactic acid raw material, and the aqueous solution was introduced to a heat exchanger. 2% thereof was vaporized in the heat exchanger, and the liquid not vaporized was recirculated (9).

The flow rate of the recirculated liquid was introduced to a decomposition tank (400), and a lactic acid oligomer was decomposed by the water included in the liquid aqueous lactic acid solution (3). The lactic acid oligomer produced in the heat exchanger was partially decomposed in the decomposition tank and introduced again to the heat exchanger. The vaporized gas-phase lactic acid stream was used as a reactor feed.

The operation process of Comparative Example 2 is shown in FIG. 3, and as illustrated in FIG. 3, flow rates of the liquid aqueous lactic acid solution (3), the aqueous solution (4) of the step 1, the third aqueous lactic acid solution (9) and the fifth lactic acid vapor (7), and a composition of each stream are as shown in the following Table 2.

TABLE 2

| Stream No. | | 1 | 2 | 3 | 4 | 7 | 9 |
|---|---|---|---|---|---|---|---|
| Flow Rate (kg/hr) | | 455 | 545 | 1000 | 51000 | 1000 | 50000 |
| Composition | Water | 0.149 | 1.000 | 0.602 | 0.022 | 0.604 | 0.018 |
| | Lactic Acid | 0.612 | 0.000 | 0.380 | 0.275 | 0.362 | 0.239 |
| | Lactic Acid Oligomer | 0.239 | 0.000 | 0.018 | 0.702 | 0.033 | 0.743 |

Comparative Example 3

Some of the water (2) was replaced by steam when a lactic acid raw material (1) was diluted in water (2), and the rest of the conditions were the same as in Comparative Example 2. This has an advantage of reducing a dilution tank size since a temperature of the dilution tank (300) increases, however, each flow rate and composition were the same as in Table 2 of Comparative Example 2.

Example 1

When diluting a purified lactic acid raw material in water, a small amount of water was introduced unlike in Comparative Example 1 so that a liquid aqueous lactic acid solution having 56% of the lactic acid raw material was prepared, and The heat exchanger had a pressure of 1.5 bar, a temperature of 238° C. and a calorie (amount of heat) of 0.5 MMkcal/hr.

The operation process of Example 1 is shown in FIG. 1, and as illustrated in FIG. 1, flow rates of the liquid aqueous lactic acid solution (3), the first aqueous lactic acid solution (4), the second lactic acid vapor (5), the absorption liquid (water) (6), the fourth aqueous lactic acid solution (8), the third aqueous lactic acid solution (9) and the fifth lactic acid vapor (7), and a composition of each stream are as shown in the following Table 3.

TABLE 3

| Stream No. | | 1 | 2 | 3 | 4 | 5 | 6 | 8 | 7 | 9 |
|---|---|---|---|---|---|---|---|---|---|---|
| Flow Rate (kg/hr) | | 455 | 445 | 900 | 51140 | 1140 | 100 | 1000 | 240 | 50000 |
| Composition | Water | 0.149 | 1.000 | 0.558 | 0.013 | 0.444 | 1.000 | 0.023 | 0.601 | 0.003 |
| | Lactic Acid | 0.612 | 0.000 | 0.418 | 0.070 | 0.458 | 0.000 | 0.548 | 0.391 | 0.061 |
| | Lactic Acid Oligomer | 0.239 | 0.000 | 0.024 | 0.917 | 0.098 | 0.000 | 0.430 | 0.008 | 0.936 | the aqueous solution was introduced to a heat exchanger. The remaining water was used as an absorption liquid, and a total amount of the introduced water was maintained the same so that the concentration of the lactic acid of the reactor feed was maintained the same at 40%.

2% thereof was vaporized in the heat exchanger, and the liquid not vaporized was recirculated and introduced back to the heat exchanger. The gas-phase lactic acid stream vaporized in the heat exchanger includes water, lactic acid and a lactic acid oligomer, and was introduced to an absorption device after that. An absorption liquid was introduced to the absorption device and absorbed and separated the oligomer in the gas phase, and the water and the lactic acid went out in a gas phase (fifth lactic acid vapor) and used as a reactor feed. The flow rate of the recirculated liquid was approximately 50 times that of the liquid aqueous lactic acid solution (No. 3 stream of FIG. 1).

Example 2

An operation was conducted in the same manner as in Example 1 except that an aqueous lactic acid solution was used instead of water as the absorption liquid.

The heat exchanger had a pressure of 1.5 bar, a temperature of 231° C. and a calorie of 0.5 MMkcal/hr.

As in Example 1, the operation process of Example 2 was also conducted as in FIG. 1, and flow rates of the liquid aqueous lactic acid solution (3), the first aqueous lactic acid solution (4), the second lactic acid vapor (5), the absorption liquid (aqueous lactic acid solution) (6), the fourth aqueous lactic acid solution (8), the third aqueous lactic acid solution (9) and the fifth lactic acid vapor (7), and a composition of each stream are as shown in the following Table 4.

TABLE 4

| Stream No. | | 1 | 2 | 3 | 4 | 5 | 6 | 8 | 7 | 9 |
|---|---|---|---|---|---|---|---|---|---|---|
| Flow Rate (kg/hr) | | 409 | 491 | 900 | 49240 | 1093 | 100 | 192 | 1001 | 48148 |
| Composition | Water | 0.149 | 1.000 | 0.602 | 0.015 | 0.499 | 0.602 | 0.022 | 0.600 | 0.004 |
| | Lactic Acid | 0.612 | 0.000 | 0.380 | 0.081 | 0.418 | 0.380 | 0.541 | 0.390 | 0.073 |
| | Lactic Acid Oligomer | 0.239 | 0.000 | 0.018 | 0.904 | 0.084 | 0.018 | 0.437 | 0.010 | 0.923 |

The composition and the content of the final lactic acid vapor before being supplied to the reactor feed (No. 7 stream in each of FIG. 1 to FIG. 3) produced according to each of Comparative Example 1, Comparative Example 2, Example 1 and Example 2 are shown in the following Table 5.

TABLE 5

| | Fifth Lactic Acid Vapor (Final Lactic Acid Vapor Supplied to Reactor Feed) | | | |
| | Comparative Example 1 | Comparative Example 2 | Example 1 | Example 2 |
|---|---|---|---|---|
| Water | 0.607 | 0.604 | 0.601 | 0.600 |
| Lactic Acid | 0.337 | 0.362 | 0.391 | 0.390 |
| Oligomer | 0.056 | 0.033 | 0.008 | 0.010 |

As seen from Table 5, it was identified that the lactic acid raw material (total content of lactic acid and lactic acid oligomer) was approximately 39 wt % in Comparative Example 1, however, the lactic acid content therein was just 85% in the lactic acid raw material, and the rest is the lactic acid oligomer. It was identified that the lactic acid oligomer content was high with the content being approximately 14%.

In Comparative Example 2 of Table 5, it was identified that the oligomer content decreased compared to in Comparative Example 1. This is due to the fact that the process of decomposing the oligomer through the decomposition tank was added, however, as identified in Table 5, the ratio of the lactic acid oligomer was still approximately 8.5%, and it was identified that a significant amount of the lactic acid oligomer was included in the fifth lactic acid vapor itself.

In Comparative Example 3, some of the water (2) was replaced by steam when the lactic acid raw material (1) was diluted in water (2), and the rest of the conditions were the same as in Comparative Example 2. This has an advantage of reducing a dilution tank size since a temperature of the dilution tank (300) increases, however, each flow rate and composition were the same as in Comparative Example 2, and the ratio of the lactic acid oligomer was still approximately 8.5%, and it was identified that a significant amount of the lactic acid oligomer was included in the fifth lactic acid vapor itself.

Example 1 of Table 5 went through the absorption process according to the disclosure of the present application, and therein, water was used as the absorption liquid. The lactic acid raw material (lactic acid and lactic acid oligomer) was included in 40 wt % as in Comparative Example 1, and it was identified that the lactic acid oligomer content in the reactor feed decreased with the lactic acid ratio being 98% and the lactic acid oligomer ratio being 2% based on the lactic acid raw material.

In addition, Example 2 of Table 5 went through the absorption process according to the disclosure of the present application, and therein, an aqueous lactic acid solution was used as the absorption liquid. The lactic acid raw material (lactic acid and lactic acid oligomer) was included in 40 wt % as in Example 1, and it was identified that the lactic acid oligomer content in the reactor feed decreased with the lactic acid ratio being 99% and the lactic acid oligomer ratio being 1% based on the lactic acid raw material.

In other words, it was identified that, by adding the process of supplying the absorption liquid to the gas-phase aqueous lactic acid solution vaporized through the heat exchanger in the process for producing acrylic acid according to one embodiment of the present application, the lactic acid oligomer included in the gas-phase aqueous lactic acid solution was absorbed, and the content of the oligomer was reduced in the aqueous lactic acid solution before being supplied to the reactor feed.

Particularly, it was identified that, by absorbing the oligomer included in the lactic acid vapor (second lactic acid vapor), which was vaporized by going through the heat exchanger, through the absorption process, the content of the lactic acid oligomer was reduced in the lactic acid vapor reducing a fouling phenomenon in the vaporizer and the reaction unit, and by including a high-content lactic acid monomer, a yield of produced acrylic acid increased and loss was minimized, increasing economic feasibility.

In addition, a decrease in the lactic acid oligomer content in the vaporized lactic acid vapor can also occur when supplying an absorption liquid before the step of going through the heat exchanger, however, a separate decomposition device is required in such a process, and a disadvantage of increasing the size of the decomposition device is also present since a residence time necessary for the decomposition is required.

In addition, when comparing with the case of supplying steam as the absorption liquid before the step of going through the heat exchanger, there is an effect of reducing the amount of energy used, however, the disclosure of the present application has significantly superior properties in terms of reducing the oligomer content in the feed compared to the case of supplying steam.

The invention claimed is:

1. A process for producing acrylic acid, the process comprising:
   (step 1) preparing a first aqueous lactic acid solution by diluting a lactic acid raw material with water;
   (step 2) heat exchanging the first aqueous lactic acid solution to form a vaporized second lactic acid vapor and an unvaporized third aqueous lactic acid solution;
   (step 3) including the unvaporized third aqueous lactic acid solution in the aqueous solution of the step 1; and
   (step 4) supplying and absorbing an absorption liquid to the vaporized second lactic acid vapor to form an absorbed fourth aqueous lactic acid solution and an unabsorbed fifth lactic acid vapor,
   wherein the absorption liquid is water or an aqueous lactic acid solution,
   wherein the step 4 includes a process of absorbing through an absorption device; and
   the absorption device has an inner pressure of greater than or equal to 0.3 bar and less than or equal to 3 bar and an inner temperature of higher than or equal to 100° C. and lower than or equal to 230° C.

2. The process of claim 1, wherein the step 2 includes a process of heat exchanging through a heat exchanger; and
   the heat exchanger has an inner pressure of greater than or equal to 0.3 bar and less than or equal to 3 bar and an inner temperature of higher than or equal to 150° C. and lower than or equal to 300° C.

3. The process of claim 1, wherein the first aqueous lactic acid solution includes water and a lactic acid raw material;
   the lactic acid raw material includes lactic acid and a lactic acid oligomer; and
   the lactic acid raw material is included in greater than or equal to 30 parts by weight and less than or equal to 99 parts by weight based on 100 parts by weight of the first aqueous lactic acid solution.

4. The process of claim 3, wherein a ratio of the lactic acid:lactic acid oligomer in the first aqueous lactic acid solution is from 1:99 to 30:70.

5. The process of claim 1, wherein a ratio of lactic acid:lactic acid oligomer in the second lactic acid vapor is from 80:20 to 95:5.

6. The process of claim 1, wherein a ratio of lactic acid:lactic acid oligomer in the fifth lactic acid vapor is from 100:0 to 90:10.

7. The process of claim 1, wherein the fifth lactic acid vapor includes water and a lactic acid raw material;

the lactic acid raw material includes lactic acid and a lactic acid oligomer; and the lactic acid raw material is included in greater than or equal to 10 parts by weight and less than or equal to 80 parts by weight based on 100 parts by weight of the fifth lactic acid vapor.

8. The process of claim 1, further comprising including the fourth aqueous lactic acid solution in the aqueous solution of the step 1.

9. The process of claim 2, wherein the heat exchanger is one or more selected from the group consisting of a falling film evaporator, a wiped film evaporator, a thermosyphon, and a forced circulation evaporator.

10. The process of claim 1, wherein the absorption device is one or more selected from the group consisting of a drum, a spray drum, a packing column, and a tray column.

\* \* \* \* \*